US 8,689,789 B2

(12) United States Patent
Andrus et al.

(10) Patent No.: US 8,689,789 B2
(45) Date of Patent: *Apr. 8, 2014

(54) MEDICAL AEROSOL NON-DILUTING HOLDING CHAMBER

(76) Inventors: Paul G. Andrus, Ancaster (CA); Gayle R. Campbell-Andrus, Ancaster (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/567,081

(22) Filed: Aug. 5, 2012

(65) Prior Publication Data

US 2012/0298100 A1 Nov. 29, 2012

Related U.S. Application Data

(63) Continuation of application No. 12/790,652, filed on May 28, 2010, now Pat. No. 8,251,063, which is a continuation of application No. 11/209,391, filed on Aug. 24, 2005, now Pat. No. 7,726,310.

(51) Int. Cl.
*A61M 11/00* (2006.01)

(52) U.S. Cl.
USPC ............. 128/205.13; 128/200.23; 128/203.28

(58) Field of Classification Search
USPC ............. 128/205.13–205.17, 200.14, 200.23, 128/202.21, 203.28
See application file for complete search history.

(56) References Cited

U.S. PATENT DOCUMENTS 7,726,310 B2   6/2010   Andrus et al.
8,251,063 B2   8/2012   Andrus et al.

*Primary Examiner* — Steven Douglas
(74) *Attorney, Agent, or Firm* — Steven M. Greenberg; CRGO Law

(57) ABSTRACT

A medical aerosol delivery device comprises a housing having a first opening and a second opening and defining a fluid passage between the first and second openings. The housing comprising a pressurized medical aerosol canister actuator having a canister receptacle disposed within the fluid passage and having a valve chamber comprising a fine bore nozzle positioned to direct atomized medicament toward the first opening. The fluid passage includes an annular portion bypassing the canister receptacle and the housing comprises a movable closure member for selectively obstructing the fluid passage.

3 Claims, 3 Drawing Sheets

MEDICAL AEROSOL NON-DILUTING HOLDING CHAMBER

CROSS-REFERENCE TO RELATED APPLICATIONS

Figure 1:
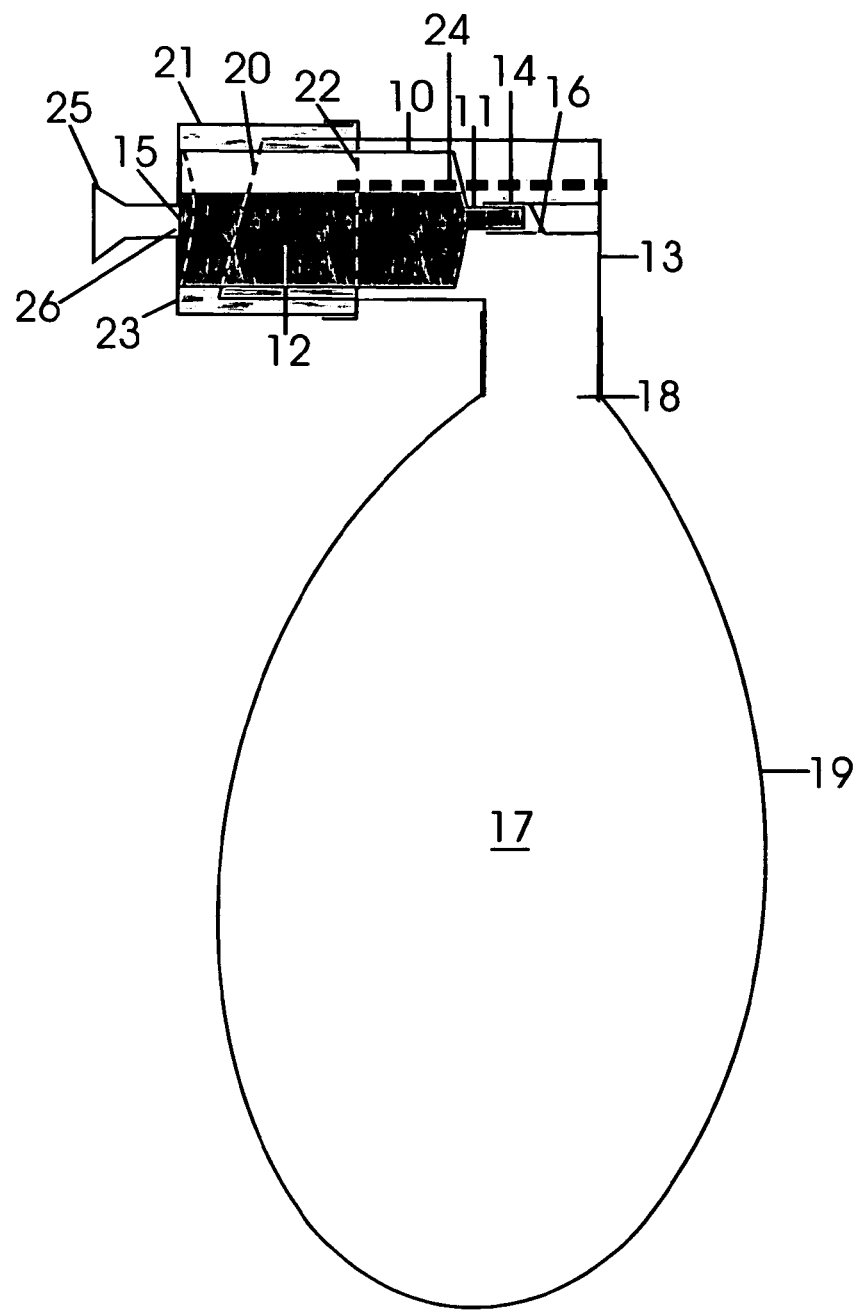
Figure 2:
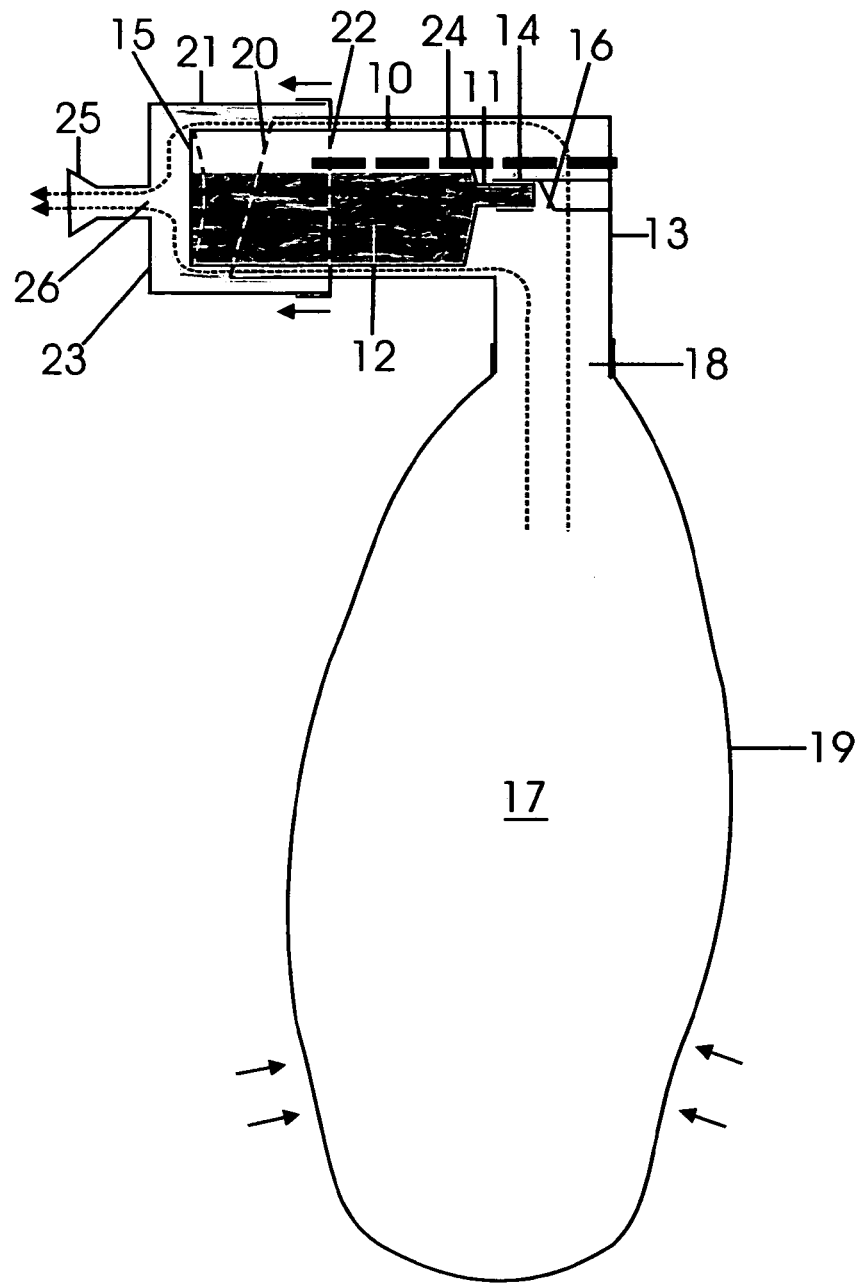
Figure 3:
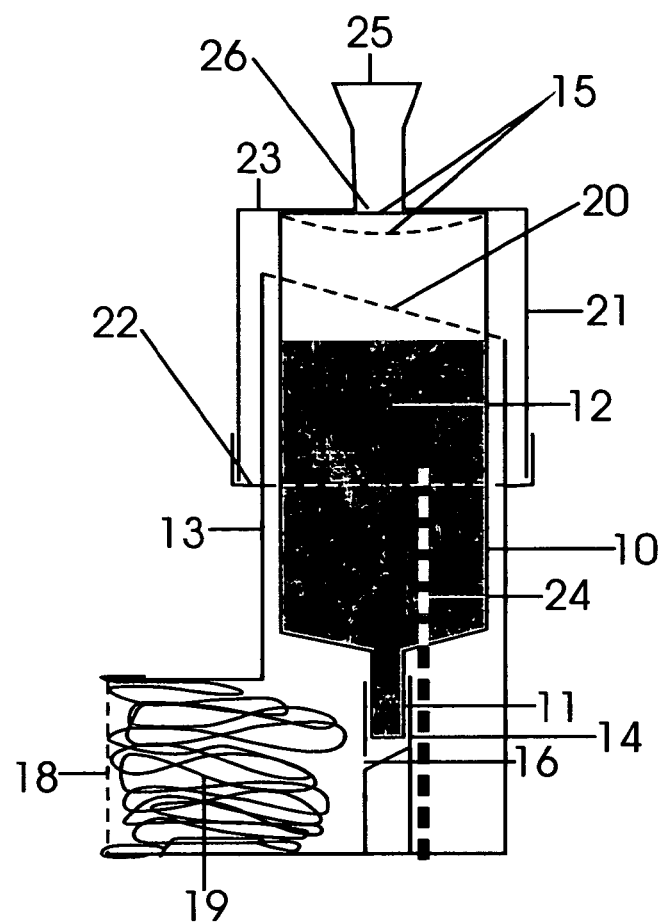

This application is a continuation of U.S. patent application Ser. No. 12/790,652 filed on May 28, 2010, now U.S. Pat. No. 8,251,063 which is a continuation of U.S. patent application Ser. No. 11/209,391 filed on Aug. 24, 2005, now U.S. Pat. No. 7,726,310.

TECHNICAL FIELD

The present disclosure relates to medical aerosol delivery devices.

BACKGROUND

Recent analysis of the public health risks and benefits of replacing cigarettes with a deep nicotine aerosol inhaler (if one were to exist) suggests that such a replacement would have a favourable impact (Sumner II W "Estimating the health consequences of replacing cigarettes with nicotine inhalers" Tobacco Control 2003; 12:124-132). The difficulties arise in developing a device that generates a sufficiently fine aerosol to allow peripheral lung delivery like that of a cigarette in a cost effective and operationally acceptable manner to current smokers, whether or not they intent to quit using nicotine. With currently available nicotine replacement therapy (gum, patch, nasal inhaler, oral vapour inhaler) most attempts at smoking cessation fail, and relapse rates remain over 75%. Many hard core smokers suffer from an underlying psychiatric problem that nicotine may help to ameliorate (Pomerleau CS "Co-factors for smoking and evolutionary psychobiology", Addiction 1997; 92:397-408). None of the available nicotine delivery devices listed above mimic a cigarette in terms of the rapid puff-by-puff delivery of an arterial bolus that reaches the brain within seconds, and this may explain why most individuals relapse to cigarette smoking While smoking, peak arterial plasma nicotine concentration may be 10 times greater than venous concentrations. It is only by absorption through the lungs that the rapid arterial bolus nicotine delivery of a cigarette can be achieved, as opposed to the relatively slower venous delivery via buccal or nasal mucosa or skin, which is characteristic of current nicotine delivery devices including the oral vapour inhaler. The key to efficient arterial (central nervous system) nicotine delivery is the particle size of the nicotine aerosol. Nicotine vapour entering the mouth condenses onto the mucosal surface of the mouth and throat. Large aerosol droplets affect the upper airway as well. Only nicotine carried by fine droplets or particles is available for absorption into the pulmonary circulation and reaches the brain quickly in high concentration. Cigarette smoke particles have a mass median aerodynamic diameter (MMAD) of 0.4 µm. Such small particles deposit mainly in the alveoli of the lung from which they may be rapidly absorbed into the pulmonary circulation.

Recent improvements in the technology of medicinal inhalers for asthma and chronic lung disease has led to the development of solution formulations for pressurised metered-dose inhalers (pMDIs) that can generate fine droplet aerosols, improving upon that of pMDIs using solid particle suspension formulations and dry powder inhaler technology which are inherently limited in their potential to go into the ultra-fine particle size range. Preliminary tests of a hydrofluoroalkane/ethanol/nicotine solution formulation pMDI has shown an MMAD of 1.5 µm (Andrus P G et. al. "Nicotine microaerosol inhaler" 1999 Canadian Respiratory Journal; Vol. 6 No 6:509-512), which is sufficiently small to allow cigarette simulating peripheral lung delivery. The hydrofluoroalkane/ethanol solution has also been developed to replace the marijuana cigarette (Davies, R. J. et al. U.S. Patent Application 20050061314 A1, Mar. 24, 2005; and Peart, J. et al. U.S. Patent Application 20040258622 A1, Dec. 23, 2004) for the same reasons as those which apply to nicotine, and in recognition of the many medicinal benefits of cannabinoids (i.e. tetrahydrocannabinol (THC)) in treating chronic pain and nausea. That is, nicotine and cannabis have been historically and are presently used most efficiently and effectively by deep inhalation, and HFA solution formulations allow the simulation of this where other inhaler technologies fall short.

The parameters of smoking (number of puffs per cigarette, number of cigarettes per day) are not random, but have been refined by user behaviour and preference over the long history of cigarette smoking for therapeutic effect. A further difficulty, however, in the simulation of smoking by inhaler is the number of puffs that are typically inhaled in the course of a day. As a result of the high efficiency of pulmonary circulation delivery by a deep inhaler or a cigarette, a unit dose of one cigarette equivalent is best delivered by several puffs over several minutes. If the entire unit dose were delivered in one puff by deep inhalation, this would be less enjoyable and potentially dangerously over stimulating to the user. The entire dose could be delivered to the upper airway in one puff, for example the buccal or nasal mucosa, because it would effectively be delivered more slowly as it is more gradually absorbed into the venous circulation. This of course forgoes the advantages and user preferences for deep inhalation as described above. pMDIs for asthma or emphysema are intended to be discharged 4 to 8 times per day giving the inhaler's 200 puffs a life of about a month. Typically a smoker inhales 10 times per cigarette for 20 cigarettes per day thereby using up one inhaler equivalent per day. This rate of inhaler expenditure is undesirable from both a cost and user acceptability standpoint.

SUMMARY

A holding chamber is used to hold a multiple-inhalation concentrated aerosol cloud which can be drawn upon several times from a single actuation of the inhaler. Holding chambers are well known and used to improve efficiency of medicinal aerosol delivery. Typically they have one way valves near the mouthpiece to allow multiple inhalations of the chamber's contents so that the dose is fully received. With each inhalation however, ambient air is drawn into the chamber and mixes freely with the remaining contents. Therefore the concentration of the medicinal aerosol drops off exponentially with successive inhalations. To satisfactorily simulate the cigarette, each inhalation should predictably be of the same concentration. With the present device, the user may draw upon a fraction of the holding chamber's contents at a time, and then deeply inhale ambient air to send the dose to the lungs. With each inhalation the chamber further collapses so that the concentration of the aerosol within the chamber remains constant. In this manner, a single actuation of a concentrated aerosol from the inhaler provides several equal inhalations, thereby greatly extending the life of the inhaler. The gradual emptying of the bag is analogous to the burning down of the cigarette. The user need not coordinate inhaler actuation with inhalation, and need not keep track of number of inhalations to get a unit dose (cigarette equivalent) as the empty bag indicates and regulates the unit dose.

In one embodiment, a pressurised metered-dose inhaler canister contains a solution formulation of nicotine or a cannabinoid in HFA propellant such that a fine microaerosol may be generated. The canister is housed within a standard L-shaped cylindrical actuator. A flexible bag aerosol holding chamber bag is sealed around the outlet passage of the actuator to receive the microaerosol upon actuation of the canister. An elastic-loaded mouthpiece is sealed around the inlet passage of the actuator so that the user may break the seal around the inlet passage by withdrawing the mouthpiece, thus allowing inhalation of a portion of the aerosol contents of the chamber. The inlet passage automatically reseals under the elastic tension as the mouthpiece is released by the user. The user subsequently draws upon the chamber's contents a number of times at a frequency analogous to smoking a cigarette until the chamber is fully collapsed, such that one inhaler actuation and one filled holding chamber are comparable to one cigarette. The holding chamber is folded and stowed within the actuator's outlet passage when not in use.

In one embodiment, a medical aerosol delivery device comprises a housing having a first opening and a second opening and defining a fluid passage between the first and second openings. The housing comprises a pressurized medical aerosol canister actuator having a canister receptacle disposed within the fluid passage and having a valve chamber comprising a fine bore nozzle positioned to direct atomized medicament toward the first opening. The fluid passage includes an annular portion bypassing the canister receptacle, and the housing comprises a movable closure member for selectively obstructing the fluid passage.

The closure member may cooperate with the actuator for releasing a metered dose of medicament.

A collapsible holding chamber may be sealingly secured to the first opening for sealing the first opening, with the first opening communicating with an interior volume of the holding chamber.

BRIEF DESCRIPTION OF THE DRAWINGS

FIG. 1 is a profile of the inhaler after inflation of the flexible holding chamber and actuation of the canister;

FIG. 2 is a profile of the inhaler during an inhalation by the user; and

FIG. 3 is profile of the inhaler while not in use showing stowage of the flexible holding chamber.

DETAILED DESCRIPTION OF THE PREFERRED EMBODIMENT

A pressurised medical aerosol canister 10 with valve 11 contains a solution formulation 12 of nicotine or a cannabinoid (i.e. THC) in hydrofluoroalkane propellant. Ethanol may also be present as a co-solvent. The canister 10 is placed in an L-shaped actuator 13 with valve chamber 14. The stem of the valve 11 sits in the valve chamber 14, such that when the valve is actuated by pressure applied to the base 15 of the canister 10, a single metered dose of the nicotine or cannabinoid solution formulation 12 is sent through a fine bore nozzle 16 in the valve chamber 14 causing a fine microaerosol cloud 17 to leave the actuator 13 via its outlet passage 18, to be held in a flexible aerosol holding chamber 19 which is air-tightly sealed in a fixed manner around the outlet orifice 18. The inlet passage 20 of the actuator 13 is air-tightly sealed in a sliding manner by an actuator cap 21 with flange 22 and baseplate 23. The flange 22 is made of semi-rigid rubber or plastic so that it may slide along the outside of the actuator 13 during actuation of the canister 10. The base plate 23 is held flatly against the base 15 of the canister 10 by an elastic cord 24 which joins the actuator cap 21 to the actuator 13. A mouthpiece 25 is connected to the cap baseplate 23 via a hole 26 in the center of the baseplate 23. The following is the method by which the device is used in the simulation of the smoking of a cigarette: Before use, the holding chamber 19 is folded in its stowed position within the outlet passage 18 of the actuator 13. Using the mouthpiece 25, the baseplate 23 is lifted from its seal with canister base 15, such that the user may inflate the holding chamber 19 by blowing air through the mouthpiece 25, into the actuator 13 around the canister 10 and then into the holding chamber 19. The mouthpiece is then released and the baseplate 23 is returned to its sealed position against the canister base 15. The baseplate 23 is then pressed towards the actuator 13 in the usual manner by which pMDIs are actuated so that a single metered dose leaves the canister 10 through the valve stem 11, into the valve chamber 14, through the nozzle 16, out through the actuator outlet passage 18, and into the pre-inflated holding chamber 19. At this point the nicotine or cannabinoid microaerosol cloud 17 is air-tightly held within the holding chamber and adjoining actuator as seen in FIG. 1. The first inhalation may then be taken by the user by using the mouthpiece 25 to again lift the baseplate 23 from its seal with the canister base 15 allowing passage by inhalation of a portion of the aerosol cloud 17 into the user's mouth. The mouthpiece 25 is then released again resealing the actuator 13 and chamber 19. The user may then take a deeper inhalation of ambient air thereby washing the nicotine or THC microaerosol deep into the lungs in the same manner as is usually done during cigarette smoking. At this point the chamber can be put down analogous to the placing of a cigarette in an ashtray as the elastic 24 maintains the air-tight seal even if a small amount of pressure is applied to the outside of the chamber 19. The user then takes 5-10 repeat inhalations from the chamber 19, until the aerosol cloud 17 is depleted and the chamber 19 fully collapsed, thus completing a cycle equivalent to smoking a single cigarette. The chamber 19 is again stuffed into the outlet passage 18 so that the device occupies only the volume of the actuator 13 for convenient pocket or purse carrying. The chamber 19 is comprised of a thin plastic bag that can be sealed around the outlet passage 18 by a circumferential elastic band around the actuator 13 at its outlet end. The bag can therefore be replaced frequently for hygienic reasons.

What is claimed is:

1. A medical aerosol delivery device, comprising:

a housing having a first opening and a second opening and defining a fluid passage between the first and second openings;

the housing comprising a pressurized medical aerosol canister actuator having a canister receptacle disposed within the fluid passage and having a valve chamber comprising a fine bore nozzle positioned to direct atomized medicament toward the first opening;

the fluid passage including an annular portion bypassing the canister receptacle;

the housing comprising a movable closure member for selectively obstructing the fluid passage.

2. The medical aerosol delivery device of claim 1, wherein the closure member cooperates with the actuator for releasing a metered dose of medicament.

3. The medical aerosol delivery device of claim 2, further comprising:

a collapsible holding chamber sealingly secured to the first opening for sealing the first opening;

the first opening communicating with an interior volume of the holding chamber.

\* \* \* \* \*